US011154255B2

(12) United States Patent
Li et al.

(10) Patent No.: US 11,154,255 B2
(45) Date of Patent: *Oct. 26, 2021

(54) METHOD FOR ANALYZING HEART RATE VARIABILITY, APPARATUS AND USE THEREOF (71) Applicants: TSINGHUA UNIVERSITY, Beijing (CN); BEIJING PINS MEDICAL CO., LTD, Beijing (CN)

(72) Inventors: Luming Li, Beijing (CN); Hongyun Liu, Beijing (CN); Zhao Yang, Beijing (CN)

(73) Assignees: TSINGHUA UNIVERSITY, Beijing (CN); BEIJING PINS MEDICAL CO.. LTD., Beijing (CN)

( * ) Notice: Subject to any disclaimer, the term of this patent is extended or adjusted under 35 U.S.C. 154(b) by 220 days.

This patent is subject to a terminal disclaimer.

(21) Appl. No.: 16/086,436

(22) PCT Filed: Aug. 4, 2017

(86) PCT No.: PCT/CN2017/095952
§ 371 (c)(1),
(2) Date: Sep. 19, 2018

(87) PCT Pub. No.: WO2018/036368
PCT Pub. Date: Mar. 1, 2018

(65) Prior Publication Data
US 2019/0125275 A1 May 2, 2019

(30) Foreign Application Priority Data
Aug. 23, 2016 (CN) .......................... 201610709242.7

(51) Int. Cl.
A61B 5/024 (2006.01)
A61B 5/00 (2006.01)
(Continued)

(52) U.S. Cl.
CPC .......... *A61B 5/7278* (2013.01); *A61B 5/0245* (2013.01); *A61B 5/02405* (2013.01);
(Continued)

(58) Field of Classification Search
CPC ................................................. A61B 5/02405
See application file for complete search history.

(56) References Cited

U.S. PATENT DOCUMENTS

2006/0189875 A1* 8/2006 Goldberger .......... A61B 5/0456
600/513

FOREIGN PATENT DOCUMENTS

CN 103251392 * 8/2013
CN 103251392 A 8/2013
(Continued)

OTHER PUBLICATIONS

Ho et al "The Prognostic Value of Non-Linear Analysis of Heart Rate Variability in Patients with Congestive Heart Failure—A Piolot Study of Multiscale Entropy", Plos One, 6(4), Apr. 13, 2011 (Apr. 2013), ISSN: 1932-6203. 2011.*
(Continued)

*Primary Examiner* — George R Evanisko
(74) *Attorney, Agent, or Firm* — Grossman, Tucker, Perreault & Pfleger, PLLC (57) ABSTRACT

A method for analyzing heart rate variability, and an apparatus and use thereof, the method for analyzing heart rate variability including collecting ECG data in vitro; digitizing and denoising the ECG data; forming the processed ECG data into a sinus NN interval sequence; selecting sinus NN interval data of 4 hours in an awake state; performing MSE calculation on the sinus NN interval sequence of 4 hours in an awake state; and extracting parameters representing the complexity of a heart rate by using MSE curves. The present invention may provide accurate and efficient screening for
(Continued)

drug-refractory epilepsy patients who are suitable for vagus nerve stimulation surgery, thus avoiding unnecessary expenses, and avoiding missing the most opportune moment for treatment. At the same time, patients suitable for VNS surgery are selected by using MSE complexity feature parameters of ECG, thus improving the overall efficacy of VNS therapy.

4 Claims, 5 Drawing Sheets

(51) Int. Cl.
    *A61B 5/0245*     (2006.01)
    *A61B 5/282*     (2021.01)
    *A61B 5/318*     (2021.01)
    *A61B 5/352*     (2021.01)
(52) U.S. Cl.
    CPC .......... *A61B 5/02438* (2013.01); *A61B 5/282* (2021.01); *A61B 5/318* (2021.01); *A61B 5/352* (2021.01); *A61B 5/4064* (2013.01); *A61B 5/4094* (2013.01); *A61B 5/6823* (2013.01); *A61B 5/7275* (2013.01)

(56) References Cited

FOREIGN PATENT DOCUMENTS

| | | |
|---|---|---|
| CN | 105476630 A | 4/2016 |
| CN | 105574322 A | 5/2016 |
| CN | 106264510 A | 1/2017 |
| CN | 106343992 A | 1/2017 |
| WO | 2013016290 A2 | 1/2013 |

OTHER PUBLICATIONS

Ho, Y.L. et al., "The Prognostic Value of Non-Linear Analysis of Heart Rate Variability in Patients with Congestive Heart Failure—A Pilot Study of Multiscale Entropy", PLoS ONE, Apr. 2011, p. 1-6, vol. 6, Issue 4; 6 pgs.

International Search Report dated Nov. 10, 2017 of corresponding International application No. PCT/CN2017/095952; 6 pgs.

* cited by examiner

METHOD FOR ANALYZING HEART RATE VARIABILITY, APPARATUS AND USE THEREOF

TECHNICAL FIELD

The invention relates to a method and an apparatus for analyzing heart rate variability and use thereof, in particular to a method for analyzing heart rate variability for patients with Vagus Nerve Stimulation (VNS) indications.

BACKGROUND

Epilepsy as a disease affects the lives of patients. For most patients, epileptic seizures could be controlled by one or more drugs. However, some patients are still not sensitive to drug treatment. These patients are called patients with drug refractory epilepsy. As an adjuvant therapy, Vagus Nerve Stimulation (VNS) can effectively control epileptic seizures in patients with drug refractory epilepsy. However, the individual differences in efficacy thereof are very large and uncertainties are pretty high. Statistical analysis shown that, epileptic seizures were completely relieved in only 5% to 9% of patients with drug refractory epilepsy who were treated with VNS surgery, about 10% of patients were completely ineffective, and the rest shown seizure frequency reduction with varying degrees. Overall, 50% reduction in seizure frequencies could be achieved in 50%-60% of patients with drug refractory epilepsy who were treated with VNS surgery. In view of uncertainties and large individual differences in the efficacy of VNS for treating drug refractory epilepsy, researchers have been trying to screen patients suitable for VNS surgery through preoperative evaluation.

At present, there has been no definitive screening method for VNS surgical indications clinically applied. Meanwhile, studies on VNS efficacy factors have been performed based on EEG (Electroencephalography, EEG), Magnetic Resonance Imaging data (MRI), patient demographic characteristics (gender, age, etc.), clinical history (disease duration), seizure characteristics (including seizure type, seizure frequency, lesion location, etc.), and the conclusions thereof are not consistent, sometimes even contradictory.

Figure 1:
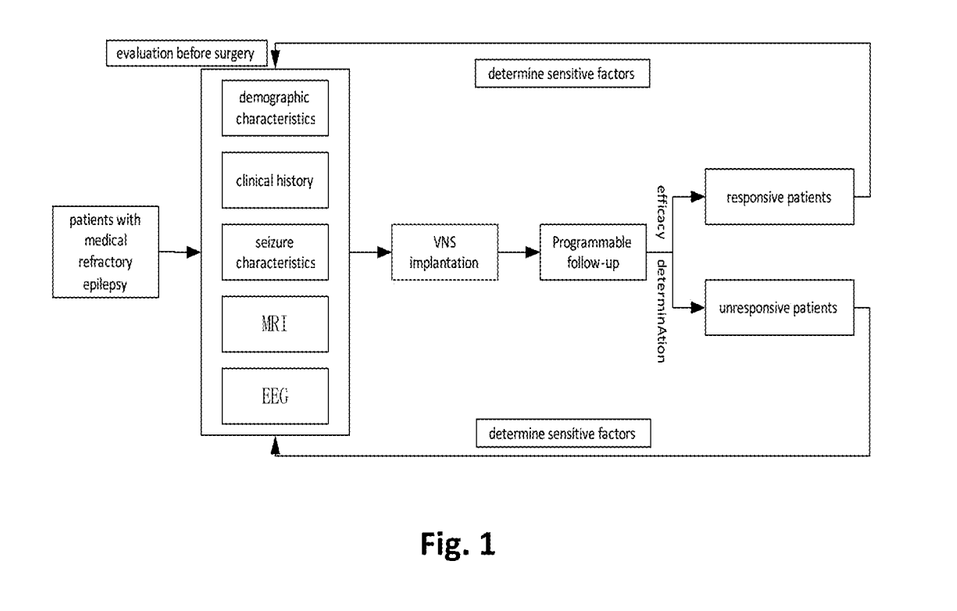
FIG. 1 is a flow chart of the prior art for screening patients with VNS indications.

The solution in the prior art is shown in FIG. 1. Firstly, systematic and comprehensive preoperative evaluations are performed for patients with drug refractory epilepsy (including demographic characteristics, medical history, seizure characteristics, MRI, EEG, etc.) before VNS surgery. Then, VNS implantation surgery is operated. After about 2 weeks, the devices are turned on. According to each patient's specific response to VNS acute stimulation, stimulation parameters are gradually adjusted in accordance with the VNS product performance and technical features, and seizure reduction of all patients are regularly analyzed. After the corresponding follow-up period (usually 1 year), the patients are classified according to reduction of seizures (i.e., efficacy). Finally, the preoperative evaluation data of patients with different efficacies are statistically analyzed, and parameters which are statistically different between patient groups are selected as sensitive factors for screening VNS patients or predicting efficacy.

The existing EEG and MRI methods have disadvantages of high cost, complicated operations, and high requirements on professional knowledge. Overall, studies based on these methods have not been clinically applied. The main reason lies in inconsistent or even contradictory conclusions for an identical problem. The method based on 24-hour dynamic ECG signals of the present invention only requires a subject to wear a portable dynamic ECG recording box, and the ECG data is collected without limiting the subject's activities, which is simple. 24-hour dynamic ECG is charged ¥240 yuan in ordinary hospital outpatients, which is relatively low, compared with long-term video electroencephalography and nuclear magnetic resonance imaging which are charged about ¥1,000 yuan. Most of all, compared with EEG and MRI, the 24-hour dynamic electrocardiogram acquisition is not limited by activities, thus is relatively simple and has good consistency.

Heart Rate Variability (HRV) refers to changes of adjacent cardiac intervals with time in Electrocardiography (ECG) signals. It originates from the autonomic nervous system's modulation of the sinus node's self-discipline, which leads to tens of milliseconds or even greater differences or fluctuations between inter-beat intervals. HRV contains a large amount of information about neurohumoral regulation, which is currently a quantitative, non-invasive and repeatable indicator for assessing activities and regulatory functions of the autonomic nervous system and the cardiovascular system. HRV analysis can indirectly reflect the interaction between sympathetic and parasympathetic nerves.

To date, there have been no studies and technical solutions for screening VNS patients using electrocardiographic signal HRV analysis technology. Epileptic diseases have a close relationship with cardiac autonomic dysfunction. With the onset and progression of epilepsy, a patient's cardiac autonomic nervous system balance is broken, which is generally manifested as increased sympathetic nerve activities and decreased parasympathetic nerve activities. Based on this conclusion, low-cost, portable and wearable signal acquisition equipment is adapted in the present invention, thus 24-hour ECG signals of an epileptic before surgery could be acquired. A multiscale entropy (MSE) of ECG could be calculated through a programmed HRV analysis, wherein characteristic parameters representing heart rate complexity are extracted on the basis of a MSE curve, thus a drug refractory epileptic suitable for VNS surgery could be accurately and efficiently screened.

SUMMARY OF THE INVENTION

The applicant found that epileptic diseases have a close relationship with cardiac autonomic dysfunction. With the onset and progression of epilepsy, a patient's cardiac autonomic nervous system balance is broken, which is generally manifested as increased sympathetic nerve activities and decreased vagus nerve activities. Moreover, it is also found that Heart Rate Variability (HRV) is a very important indicator. HRV refers to changes of adjacent cardiac intervals with time in Electrocardiography (ECG) signals. It originates from the autonomic nervous system's modulation of the sinus node's self-discipline, which leads to tens of milliseconds or even greater differences or fluctuations between inter-beat intervals. HRV contains a large amount of information about neurohumoral regulation, which is currently a quantitative, non-invasive and repeatable indicator for assessing for assessing activities and regulatory functions of the autonomic nervous system and the cardiovascular system. HRV analysis can indirectly reflect the interaction between sympathetic and parasympathetic nerves.

Based on this finding, low-cost, portable and wearable signal acquisition equipment is adapted in the present invention, thus 24-hour ECG signals of an epileptic before surgery could be acquired. A multiscale entropy (MSE) of ECG could be calculated through a programmed HRV analysis, wherein characteristic parameters representing heart rate complexity are extracted on the basis of an MSE curve, and a drug refractory epileptic suitable for VNS surgery could be accurately and efficiently screened, thus saving unnecessary expenditures and avoiding delaying the optimal timing for treatment. At the same time, a patient suitable for VNS surgery is clearly selected through characteristic parameters of ECG's MSE heart rate complexity, which could generally improve the efficacy of VNS therapy.

The present invention provides a method for analyzing heart rate variability, comprising the following steps:

1) collecting ECG data in vitro;

2) digitizing and denoising the ECG data;

3) forming the processed ECG data into a sinus NN interval data;

4) selecting sinus NN interval data of 4 hours in an awake stake;

5) performing MSE calculation on the selected 4-hour sinus NN interval sequence in an awake stake;

6) extracting parameters representing heart rate complexity by means of a MSE curve.

The specific method of steps 5)-6) is as follows:

i. performing coarse grained processing on the NN interval sequence $\{X_1, \ldots, X_i, \ldots, X_N\}$ in step 4), to obtain reconstructed sequences $$y_j^\tau = 1/\tau \sum_{i=(j-1)\tau+1}^{j\tau} x_i, 1 \le j \le N/\tau$$

with different scales, $\tau$ as a scale factor;

$$y_j^\tau = 1/\tau \sum_{i=(j-1)\tau+1}^{j\tau} x_i.$$

ii. calculating a sample entropy, for each scale's sequence iii. drawing a curve of the sample entropy with respect to the different scale factors, and obtaining characteristic parameters indicative of the heart rate complexity.

The characteristic parameters indicative of the heart rate complexity are acquired as follows:

For the curve in step iii, Slope n1 is obtained by linearly fitting points with scales of 1-n1; scales n2-n3 are segmented, and each area encompassed by each segment of the scale curve and the horizontal axis is calculated to obtain parameters Area1.

Further, n1<n2<n3, n3≤40; the number of parameters Area1 is between 1 and 7.

Further, n1=5, the slope parameter Slope is Slope 5, n2=6, n3=20. And parameters Area1 are Area1 1-5, Area1 6-15, and Area1 6-20.

Further, threshold judgment is performed for the parameters Slope and Area1.

Further, the threshold of Slope 5 is 0.071±0.002, the threshold of Area1 1-5 is 4.32±0.04, the threshold of Area1 6-15 is 10.57±0.2 and the threshold of Area1 6-20 is 15.85±0.3.

The present invention further provides a device for analyzing heart rate variability, wherein comprising a heart rate complexity calculation module, which calculates by means of the above-mentioned method.

The device further comprises one or more of a data acquisition module, a digitization processing module, a denoising module, and a judgment module.

The present invention further provides a wearable electrocardiographic monitoring apparatus, wherein comprising the above-mentioned device for analyzing heart rate variability.

EMBODIMENTS

Example 1

Figure 2:
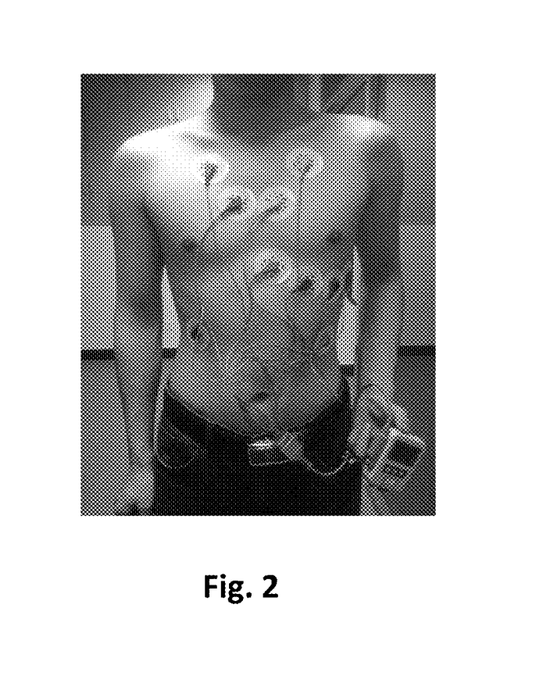
FIG. 2 is a diagram of 12-lead ECG acquisition.
Figure 3:
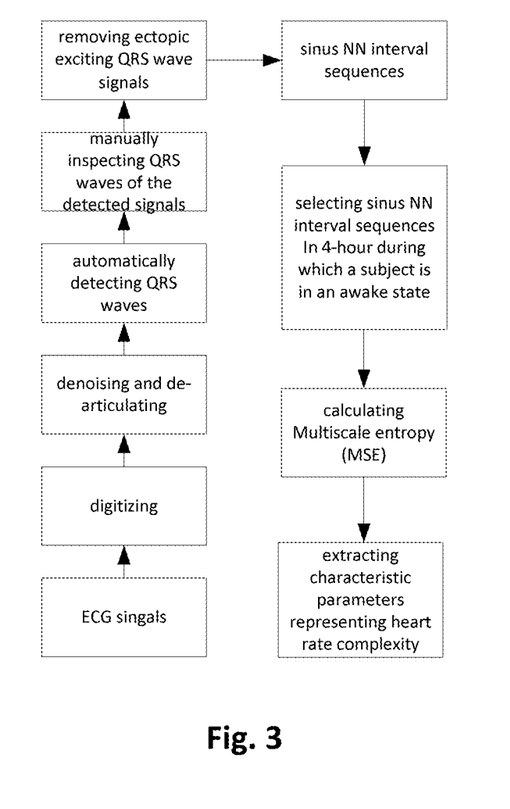
FIG. 3 is a flow chart of ECG signal processing.

As shown in FIG. 2, a standard 12-lead ECG acquisition for 24 hours before surgery requires: sampling frequency of the ECG acquisition device is greater than or equal to 500 Hz; during ECG recording, activities such as strenuous exercises and medications that could affect cardiac functions should be avoided; the recording period is 24 hours. Recording environment and conditions of subjects should be basically similar. The data used for HRV analysis should be ensured to be normal sinus NN intervals. During HRV analysis, normal sinus NN intervals of 4 hours are selected for MSE analysis from the 24-hour long-term ECG records during which the subject is in an awake state. The specific processing flow of ECG signals is shown in FIG. 3.

1) collecting and digitizing ECG signals;

2) denoising and de-articulating digital signals;

3) automatically detecting QRS waves thereof;

4) manually inspecting QRS waves of the detected signals;

5) removing ectopic exciting QRS wave signals;

6) forming a sinus NN interval sequence;

7) selecting 4-hour sinus NN interval sequences in the case of a subject in an awake state;

8) calculating MSE based on the 4-hour sinus NN interval sequences;

9) drawing a MSE curving, wherein the scale factor is as the horizontal and the entropy value corresponding to the scale factor is as the ordinate;

10) extracting characteristic parameters representing heart rate complexity, according to the MSE curve.

The MSE calculation method in the HRV analysis adopted in the present invention extracts characteristic parameters of Slope5, Area1-5, Area6-15, and Area6-20 to represent the heart rate complexity.

Figure 4:
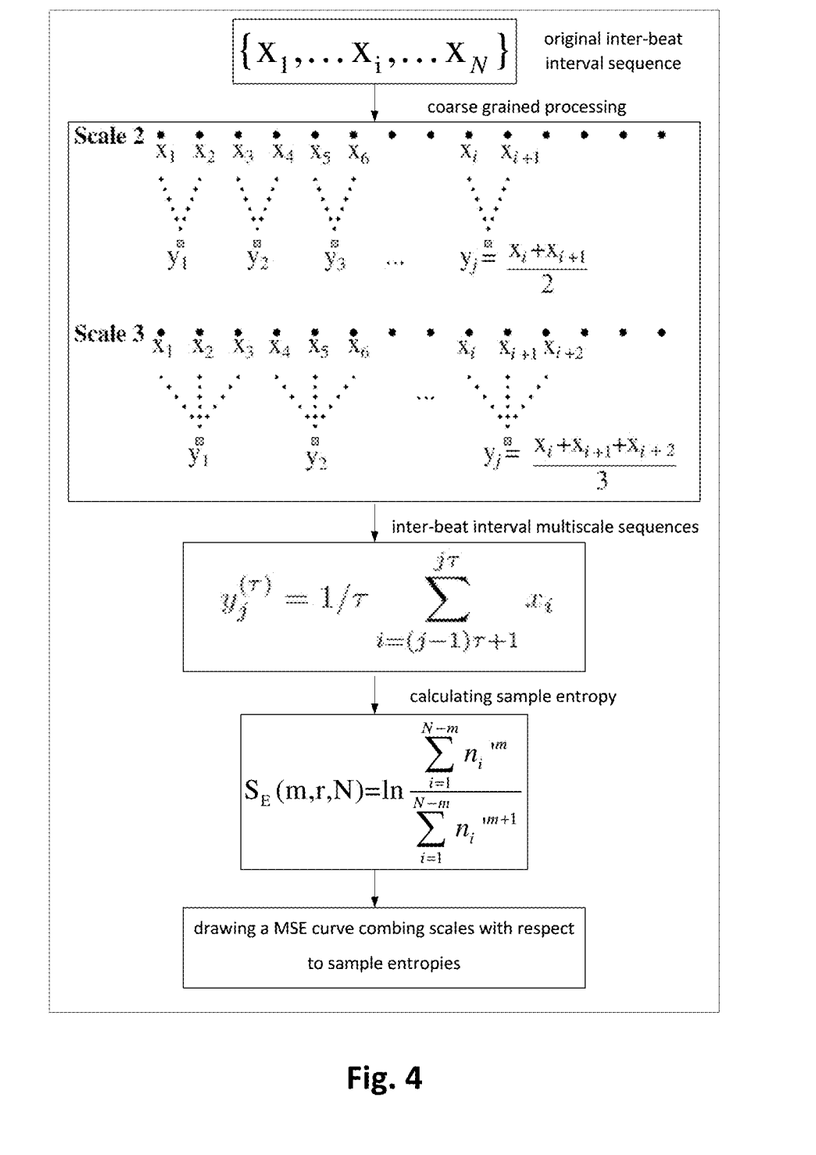
FIG. 4 is a flow chart of MSE analysis method.

The MSE method has the following steps (see FIG. 4):

(1) performing coarse grained processing on the 4-hour normal sinus NN interval sequence $\{X_1, \ldots, X_i, \ldots, X_N\}$ to obtain reconstructed sequences $$y_j^\tau = 1/\tau \sum_{i=(j-1)\tau+1}^{j\tau} x_i, 1 \le j \le N/\tau$$

with different scales, $\tau$ as a scale factor;

(2) calculating a sample entropy, for each scale's sequence $$y_j^\tau = 1/\tau \sum_{i=(j-1)\tau+1}^{j\tau} x_i;$$

Figure 5:
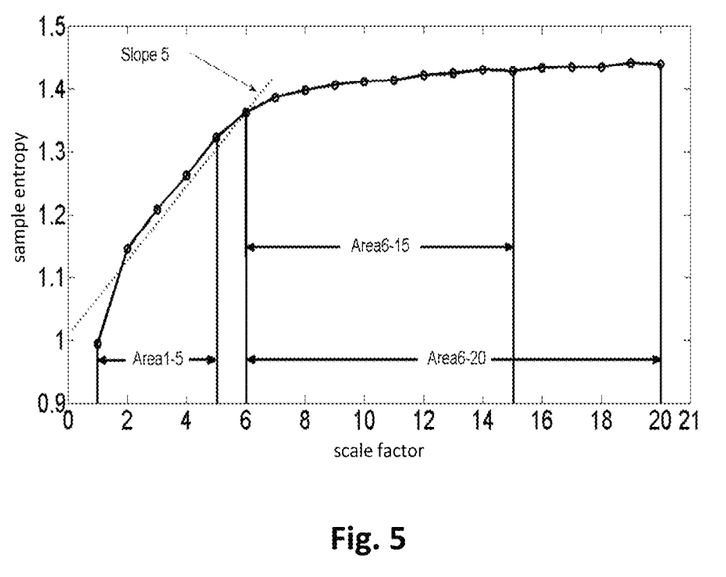
FIG. 5 is a diagram of extracting indicators of MSE Complexity.

(3) drawing a curve of the sample entropies with respect to the different scale factors, shown in FIG. 5; linearly fitting points of scales 1-5 to obtain slope 5; then calculating Area1-5, Area 6-15, and Area 6-20 encompassed by scale 1-5, scale 6-15, scale 6-20 curve and the horizontal axis, wherein, the above four parameters are characteristic parameters representing the heart rate complexity.

Figure 6:
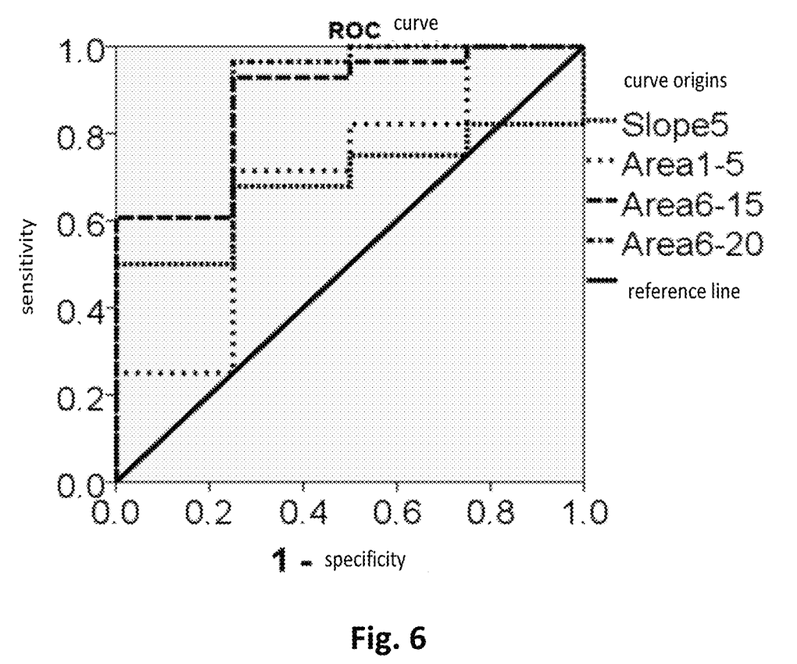
FIG. 6 is a threshold selection ROC curve
Figure 7:
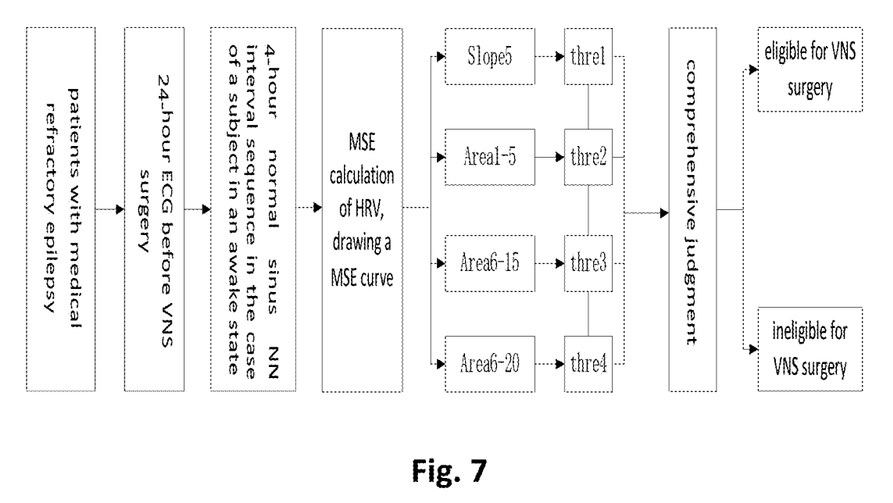
FIG. 7 is a flow chart for judgment.
Figure 8:
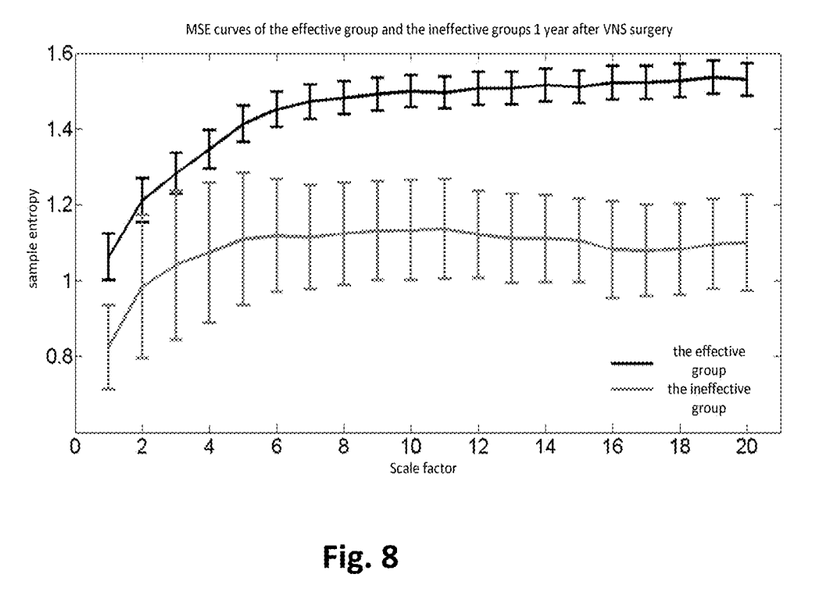
FIG. 8 shows MSE curves of the effective group and the ineffective group

For patients with drug-resistant epilepsy, 24-hour electrocardiogram acquisition was performed before surgery. The 24-hour electrocardiogram data collected was processed, according to the above-mentioned method, to obtain normal sinus NN interval sequences in 4 hours during which a subject is in an awake state. The MSE analysis was performed on the above-mentioned 4-hour NN interval sequences according to the above-mentioned method. Characteristic parameters such as Slope5, Area1-5, Area6-15, Area6-20, etc., which represent heart rate complexity, were extracted. Then comprehensive judgment selection was performed through corresponding threshold judgment (as shown in FIG. 6). The VNS surgical patients in the training set were classified according to follow-up efficacy after a certain period of time (effective group and ineffective group). The above-mentioned heart rate complexity indicators of the effective group and the ineffective group were statistically analyzed, and Receiver Operating Characteristic (ROC) curves were drawn for Slope5, Area 1-5, Area 6-15, and Area 6-20. The threshold of each indicator (Youden index) is a point in each curve which has the shortest distance to the top left corner (that is, the coordinates (1, 1)). Finally, patients who are eligible for VNS surgery and patients who are not eligible for VNS surgery are distinguished based on the corresponding threshold (as shown in FIG. 7). When the four characteristic parameters Slope5, Area1-5, Area6-15 and Area6-20, representing heart rate complexity, are used to distinguish patients eligible for VNS surgery from patients ineligible for VNS surgery respectively, their corresponding threshold value selection and their corresponding screening accuracy are as follows:

When Slope5=0.071, patients with a value higher than said value were considered eligible for VNS surgery. The screening accuracy was 67.9%.

When Area 1-5=4.32, patients with a value higher than said value were considered eligible for VNS surgery. The screening accuracy was 71.4%.

When Area6-15=10.57, patients with a value higher than said value were considered eligible for VNS surgery. The screening accuracy was 92.9%.

When Area6-20=15.85, patients with a value higher than said value were considered eligible for VNS surgery. The screening accuracy was 96.4%.

Example 2

The complexity indicator Area 6-n, when the scale factor in the MES analysis method of Example 1 is expanded to n, could also be used for screening VNS patients as described above.

In the present invention, for patients with drug refractory epilepsy, preoperative electrocardiogram acquisition 24 hours before surgery and the MSE analysis of HRV were performed. In this way, patients with drug refractory epilepsy could be screened before surgery, thereby guiding patients who are not eligible for VNS therapy not to receive the surgery and choose other therapies, which could save unnecessary expenditures and avoiding delaying the optimal timing for treatment. Meanwhile, patients with VNS surgical indications were clearly selected by extracting characteristic parameters representing heart rate complexity through ECG's MSE curve, which could improve overall VNS therapeutic efficacy.

Example 3

In accordance with the above screening method, 32 patients with medical refractory epilepsy, who had undergone VNS surgery at Beijing Tiantan Hospital from Aug. 13, 2014 to Dec. 31, 2014, were selected for test. Before VNS surgery, these 32 patients with medical refractory epilepsy were comprehensively evaluated (including demographic characteristics, clinical history, history of antiepileptic medication, 24-hours video-EEG, MRI, and 24-hour dynamic electrocardiogram etc.).

According to the above ECG signal processing method, the MSE analysis was performed, based on 24-hour dynamic electrocardiographic data. The corresponding characteristic parameters Slope5, Area1-5, Area6-15, and Area6-20 were extracted based on each patient's MSE curve. At the end of 1-year follow-up, among 32 patients with drug refractory epilepsy who had undergone VNS treatment, 28 patients' seizure frequencies had been reduced to various degrees (seizures had been completely controlled in 6 patients), who were considered as the effective group, and the remaining 4 patients' seizure frequencies after VNS surgery hadn't changed compared with those before VNS surgery, who were considered as the ineffective group. The MSE curves of the effective group and the ineffective group differ greatly, which suggested that the MSE method could be adapted to screen patients with VNS indications. Furthermore, each patient's characteristic parameters Slope5, Area1-5, Area6-15, and Area6-20 before surgery could be adapted to predict efficacy. The results shown that, among the above four parameters, Area6-20 was the most accurate parameter: when its threshold was set to 15.85, only one patient's Area6-20 was 15.09 among the 28 effective patients, as shown in Table 1, and the rest patients' Area6-20 were greater than 15.85. The screening accuracy-rate exceeded 96%, which confirmed that the MSE method of the above HRV analysis could accurately and effectively screen patients with VNS indications.

TABLE 1

|  |  | Slope5 | Area1-5 | Area6-15 | Area6-20 |
|---|---|---|---|---|---|
| Effective group | patient1 | 0.141 | 5.651 | 14.074 | 21.871 |
|  | patient2 | 0.098 | 2.925 | 9.587 | 15.093 |
|  | patient3 | 0.012 | 7.596 | 16.155 | 24.702 |
|  | patient4 | 0.069 | 5.341 | 14.477 | 23.084 |
|  | patient5 | 0.081 | 4.531 | 10.915 | 17.081 |
|  | patient6 | 0.045 | 6.766 | 16.296 | 25.248 |
|  | patient7 | 0.092 | 4.150 | 11.503 | 18.059 |
|  | patient8 | 0.101 | 3.685 | 11.804 | 18.769 |
|  | patient9 | 0.091 | 6.962 | 17.257 | 27.045 |
|  | patient10 | 0.177 | 3.983 | 14.009 | 22.139 |
|  | patient11 | 0.169 | 5.571 | 14.666 | 23.090 |
|  | patient12 | 0.116 | 5.529 | 15.255 | 23.922 |
|  | patient13 | 0.112 | 4.124 | 11.135 | 17.381 |
|  | patient14 | 0.144 | 4.189 | 12.097 | 19.044 |
|  | patient15 | 0.099 | 4.953 | 12.932 | 20.050 |
|  | patient16 | 0.070 | 5.904 | 13.657 | 21.414 |
|  | patient17 | 0.172 | 4.599 | 11.162 | 16.557 |
|  | patient18 | −0.024 | 5.839 | 13.736 | 21.497 |
|  | patient19 | 0.098 | 6.115 | 15.443 | 23.849 |
|  | patient20 | −0.066 | 5.197 | 11.964 | 19.043 |
|  | patient21 | 0.072 | 3.875 | 10.273 | 16.025 |
|  | patient22 | 0.087 | 5.132 | 14.689 | 23.120 |
|  | patient23 | 0.101 | 6.058 | 15.677 | 24.371 |
|  | patient24 | 0.053 | 4.871 | 14.701 | 23.563 |
|  | patient25 | 0.128 | 5.580 | 15.252 | 23.891 |
|  | patient26 | −0.041 | 5.299 | 13.201 | 20.832 |
|  | patient27 | 0.107 | 4.417 | 13.854 | 21.959 |
|  | patient28 | 0.030 | 3.322 | 10.847 | 17.468 |
| Ineffective group | patient29 | 0.070 | 4.226 | 9.647 | 14.219 |
|  | patient30 | 0.093 | 5.740 | 12.949 | 20.118 |
|  | patient31 | 0.033 | 2.257 | 7.488 | 12.139 |
|  | patient32 | 0.068 | 4.043 | 10.298 | 15.680 |

The above description is only preferred embodiments of the present invention. It should be noted that, those skilled in the art can make improvements and modifications, without departing from the principle of the present invention. These improvements and modifications should be regarded in the scope of the present invention. In addition, although specific terms are used in this description, these terms are merely for convenience of illustration and do not constitute any limitation to the present invention.

The invention claimed is:

1. A computer-implemented method for analyzing heart rate to identify a patient with drug-resistant epilepsy suitable for Vagus Nerve Stimulation (VNS) surgery comprising:
   collecting electrocardiography (ECG) data in vitro for the patient with drug-resistant epilepsy;
   digitizing and denoising the ECG data;
   forming the digitized and denoised ECG data into a sinus NN interval data;
   selecting a portion of sinus NN interval data from the formed sinus NN interval data corresponding to a first period of time, the first period of time being while the first patient was in an awake state;
   performing a multiscale entropy (MSE) calculation on the selected sinus NN interval data in the awake state, comprising:
     performing coarse grained processing on the selected portion of sinus NN interval data $\{X_1, \ldots, x_i, \ldots, x_N\}$ and obtaining therefrom reconstructed sequences using a plurality of different scale factors and an equation defined as $$y_j^\tau = 1/\tau \sum_{i=(j-1)\tau+1}^{j\tau} x_i, \ 1 \leq j \leq N/\tau,$$

with τ as a given scale factor of the plurality of different scale factors, and the plurality of different scale factors including scales 1-20;
   calculating a sample entropy for each reconstructed sequence with a different scale factor τ;
   drawing a MSE curve of the sample entropy with respect to the plurality of different scale factors with the plurality of different scale factors being along a horizontal axis and the sample entropy as a vertical axis, the curve having a plurality of segments corresponding to a respective one of the plurality of different scale factors;
   1) extracting parameters representing a heart rate complexity based on the MSE curve, wherein extracting parameters representing the heart rate complexity based on the MSE curve comprises:
     for the curve of the sample entropy, obtaining a slope parameter by linearly fitting points of the curve that correspond with the scale 1 to scale 5;
     dividing the curve from the scale 1 to the scale 20 into a plurality of segments; and calculating Area parameters for each area encompassed by each segment of the plurality of segments of the curve to obtain the parameters representing heart rate complexity;
   2) determining thresholds for the parameters representing heart rate complexity, the thresholds to identify patients with drug-resistant epilepsy suitable for VNS surgery, and identifying a second patient with drug-resistant epilepsy suitable for VNS surgery based on the thresholds;
   wherein the Area parameters are Area 1-5 which is based on scale 1 to scale 5, Area 6-15 which is based on scale 6 to scale 15, and Area 6-20 which is based on scale 6 to scale 20;
   wherein the threshold of the slope parameter is 0.071±0.002, the threshold of Area 1-5 is 4.32±0.04, the threshold of Area 6-15 is 10.57±0.2 and the threshold of Area 6-20 is 15.85±0.3.

2. The method of claim 1, wherein identifying the second patient with a drug-resistant epilepsy suitable for VNS surgery is further based on performing a multiscale entropy (MSE) calculation on the ECG data of the second patient, the MSE calculation to generate a corresponding curve; and wherein the method further comprises:
   extracting the Slope parameter and Area parameters for the second patient; and
   determining the second patient is eligible for VNS surgery based on the one or more parameters having an associated value that exceeds a corresponding threshold value of the thresholds for the extracted parameters representing heart rate complexity.

3. A device comprising:
   a monitoring apparatus configured to:
     collect electrocardiography (ECG) data in vitro for a first patient with drug-resistant epilepsy;
     digitize and denoising the ECG data;
     format the digitized and denoised ECG data into a sinus NN interval data;
     select a portion of sinus NN interval data from the formatted sinus NN interval data corresponding to a first period of time, the first period of time being while the first patient was in an awake state;

perform a multiscale entropy (MSE) calculation on the selected sinus NN interval data in the awake state based on:
  performing coarse grained processing on the selected portion of sinus NN interval data $\{X_1, \ldots, x_i, \ldots, x_N\}$ and obtaining therefrom reconstructed sequences using a plurality of different scale factors and an equation defined as $$y_j^\tau = 1/\tau \sum_{i=(j-1)\tau+1}^{j\tau} x_i, 1 \le j \le N/\tau,$$

with $\tau$ as a given scale factor and the plurality of different scale factors including scales 1-20;
  calculating a sample entropy for each reconstructed sequence with a different scale factor $\tau$;
  drawing an MSE curve of the sample entropy with respect to the plurality of different scale factors with the plurality of different scale factors being along a horizontal axis and the sample entropy along a vertical axis and the curve having a plurality of segments corresponding to a respective one of the plurality of different scale factors;
  extracting parameters representing a heart rate complexity based on the MSE curve, wherein extracting parameters representing the heart rate complexity based on the MSE curve comprises:
    for the MSE curve of the sample entropy, obtaining a slope parameter by linearly fitting points of the MSE curve that correspond with the scale 1 to scale 5;
    dividing the curve from the scale 1 to the scale 20 into a plurality of segments;
    calculating Area parameters for each area encompassed by each segment of the plurality of segments of the curve to obtain the parameters representing heart rate complexity;
  determining thresholds for the parameters representing heart rate complexity, the thresholds for identification of a second patient with drug-resistant epilepsy suitable for VNS surgery, the second patient different than the first patient;
  identifying the second patient with drug-resistant epilepsy suitable for VNS surgery based on the thresholds;
  wherein the Area parameters are Area 1-5 which is based on scale 1 to scale 5, Area 6-15 which is based on scale 6 to scale 15, and Area 6-20 which is based on scale 6 to scale 20;
  wherein the threshold of the slope parameter is 0.071±0.002, the threshold of Area 1-5 is 4.32±0.04, the threshold of Area 6-15 is 10.57±0.2 and the threshold of Area 6-20 is 15.85±0.3.

4. The device of claim 3, wherein the monitoring apparatus is wearable.

* * * * *